United States Patent [19]

Engelhardt et al.

[11] Patent Number: 5,058,416

[45] Date of Patent: * Oct. 22, 1991

[54] APPARATUS FOR THE DETERMINATION OF THE PARTIAL PRESSURE OF GASES DISSOLVED IN A FLUID

[75] Inventors: Harald Engelhardt; Guenter Rau, both of Aachen; Helmut Reul, Dueren, all of Fed. Rep. of Germany

[73] Assignee: Siemens Aktiengesellschaft, Berlin and Munich, Fed. Rep. of Germany

[*] Notice: The portion of the term of this patent subsequent to Feb. 22, 2006 has been disclaimed.

[21] Appl. No.: 293,620

[22] Filed: Jan. 5, 1989

Related U.S. Application Data

[63] Continuation of Ser. No. 64,014, Jun. 19, 1987, abandoned.

[30] Foreign Application Priority Data

Jun. 21, 1986 [DE] Fed. Rep. of Germany ....... 3620873

[51] Int. Cl.$^5$ ................................................. A61B 5/00
[52] U.S. Cl. ..................................... 73/19.01; 128/632
[58] Field of Search ................. 73/19, 863.23; 128/632

[56] References Cited

U.S. PATENT DOCUMENTS

| 3,518,982 | 7/1970 | Timmins et al. | 128/632 |
| 3,658,053 | 4/1972 | Fergusson et al. | 128/632 |
| 3,983,864 | 10/1976 | Sielaff et al. | 128/632 |
| 4,274,417 | 6/1981 | Delpy | 128/632 |
| 4,516,580 | 5/1985 | Polanyi | 73/19 X |

FOREIGN PATENT DOCUMENTS 851172 7/1981 U.S.S.R. ........................... 73/863.23

OTHER PUBLICATIONS

Massaro et al., *Non-Polarographic Blood Gas Analysis*, In Biomat. Med. Dev., vol. 4:(3-4), pp. 385-396, 1976.

Primary Examiner—Tom Noland
Assistant Examiner—Joseph W. Roskos
Attorney, Agent, or Firm—Hill, Van Santen, Steadman & Simpson

[57] ABSTRACT

An apparatus for determining the partial pressure of a gas dissolved in a fluid which includes a catheter consisting of a double bored coaxial catheter having an outer tube and a spaced coaxial inner tube, the outer tube being permeable to the gas being measured, together with a pump for delivering a continuous flow of a carrier fluid into the space between the inner tube and the outer tube. A measuring device is located downstream of the catheter for determining the partial pressure of the gas in the carrier fluid. A mass transfer unit receives the gas after the measuring device and is arranged to bring the partial pressure of the gas in the carrier fluid to a predetermined value.

18 Claims, 5 Drawing Sheets

APPARATUS FOR THE DETERMINATION OF THE PARTIAL PRESSURE OF GASES DISSOLVED IN A FLUID

This is a continuation of application Ser. No. 064,014, filed June 19, 1987, now abandoned.

BACKGROUND OF THE INVENTION

1. Field of the Invention

The present invention is directed to an apparatus for determining the partial pressure of a gas utilizing a double bored catheter whose outer tube is permeable to the gas, together with a pump for circulating a carrier fluid continuously through the space between the two tubes of the catheter, together with a measuring means for determining the partial pressure of the gas in the fluid.

2. Description of the Prior Art

Various types of apparatus for the determination of the partial pressure of gases and gas mixtures dissolved in fluids are used, for example, in medicine in the analysis of arterial blood and analysis of respiratory air. Other applications of such apparatus are to be found in environmental protection in the measurement of nitrous oxides in exhaust gases and in the measurement of the oxygen content of standing bodies of water. A still further example of the application of such apparatus is in the measurement of partial pressures in absorption processes such, for example, as in gas separating and in gas cleaning.

An apparatus of the type described will be found in German AS 25 34 255. In this known apparatus which is particularly intended for the determination of gas concentrations dissolved in blood, a catheter is introduced into the blood stream to be analyzed in the living subject. At least one part of the catheter is provided with a tubular membrane which is in direct contact with the blood, the tubular membrane being permeable by the gases and essentially impermeable by the blood. A gas which is admitted into the catheter at roughly atmospheric pressure thereby comes into contact with the membrane and is employed as a carrier fluid. After an equilibrium between the carrier gas and the gases dissolved in the blood has been established, the gas mixture is removed from the catheter and analyzed.

This known apparatus has a number of disadvantages. The use of gas as a carrier fluid represents a certain safety risk upon catheter failure, since the carrier gas can then proceed directly into the blood circulation. Furthermore, the known apparatus permits only a discontinuous measurement since one must wait first for the equilibrium between the carrier gas and the gases dissolved in the blood to be established and then a specimen can be removed from the catheter to be analyzed in a separate unit.

SUMMARY OF THE INVENTION

The present invention provides an apparatus for the determination of the partial pressure of gases and gas mixtures dissolved in fluids wherein a continuous determination of the partial pressure is possible. The apparatus of the invention comprises a catheter of the double bored coaxial type having an outer tube and a spaced coaxial inner tube, the outer tube being permeable to the gas. A fluid circulating means is provided for delivering a continuous flow of a carrier fluid into the space between the inner tube and the outer tube. A measuring means is located downstream of the catheter for determining the partial pressure of the gas in the carrier fluid. A mass transfer unit receives the gas after passage through the measuring means and brings the partial pressure of the gas in the carrier fluid to a predetermined value.

The outer tube may be permeable to more than one of the gases dissolved in the fluid or it may be selectively permeable to one of the gases. The space between the outer and inner tubes of the catheter may be divided into separate channels over at least a portion of the lengths of the tubes.

The inner tube is substantially impermeable to the dissolved gas. In a preferred form of the invention, the fluid circulating means comprises a closed circulating system and the carrier fluid is a liquid.

In operation, the carrier fluid flowing through the inner tube of the catheter emerges from the inner tube at the front end region and flows back through the clearance between the outer and inner tubes. It subsequently flows through the measuring means for determining partial pressure and through the mass transfer unit in which the carrier fluid enriched with gas is stripped to a defined partial pressure of the gas or gases. Subsequently, the stripped carrier fluid returns into the inner tube. It is possible, of course, to reverse the flow direction of the carrier fluid.

The apparatus has the advantage that a continuous measurement of the partial pressures can be obtained without further difficulty, since the carrier fluid with the gases dissolved in it continuously flows through the measuring means.

The present invention proceeds on the basis of the fundamental idea that it is not necessary to wait for equilibrium between the fluid in which the gases are dissolved and the carrier fluid to exist. On the contrary, with an apparatus wherein the catheter is a double bored catheter employing circulating flow, it is possible without further means to determine the partial pressure of the gas from the low partial pressure measured in the conveying fluid.

In addition to the possibility of continuous measurement of the partial pressures, the apparatus of the present invention also has a number of further advantages which particularly adapt it for employment in blood gas analysis.

The determination of arterial partial oxygen pressure is included in the most important laboratory diagnostic examinations in the clinical treatment of respiratory and metabolic disturbances, in addition to the identification of the pH value and of the base excess. The relationship between the partial oxygen pressure and the oxygen concentration of the blood is established by the oxygen bonding curve. With a known pH value, the partial oxygen pressure and partial carbon dioxide pressure, all of the important data of the acid-base status can be completely identified.

The apparatus of the present invention has a number of advantages when used in conjunction with a living subject. For one, a liquid such as water or a saline solution in which the gas to be identified dissolves can be employed as the carrier fluid so that there is no safety risk even upon catheter failure. As a result of the continuous stream of carrier fluid passing through the apparatus in a closed circulatory system, all sterilization problems are eliminated. The carrier fluid passing through the apparatus is sterilized only once before introduction into the blood vessel. Risks which could occur due to the replenishment of new carrier fluid are completely eliminated.

Depending on the application, it is also possible to design the outer tube of the catheter either permeable for all gases dissolved in the fluid or selectively permeable in order to achieve a "pre-selection".

The clearance between the outer tube and the inner tube of the catheter can be divided into a plurality of individual channels or capillaries which are connected to separating measuring systems. This enables the measurement of a flow distribution or employing channel walls which are selectively parting membranes, enables the separation of the various gases contained in the fluid.

In any case, it is advantageous to have the inner tube of the catheter gas-impermeable.

The circulating means may take the form of a pump or a compressor but other devices can also be used.

The measuring means may take the form of a wide variety of apparatus for determining the partial pressure. For example, mass spectrometers and/or gas chromatographs can be employed as the measuring means. The apparatus, however, is particularly suited for measuring devices which comprise an electrode operating on the polarographic principles. The advantage of such polarographic electrodes is that they are reliable simple to manipulate, and relatively inexpensive and, beyond this, have a short response time. A further advantage is derived in that the S-shaped curve of the oxygen bonding curve is extremely flat in arterial blood upon determination of the partial oxygen pressure. The result is that extremely great changes in the partial oxygen pressure in this region merely cause extremely small changes in the oxygen concentration of the blood. An impending insufficient supply of oxygen can thus be identified considerably better with reference to the change of the partial pressure than can be identified with a direct determination of the oxygen concentration.

In traditional apparatus, polarographic electrodes have the disadvantage that the specimen to be examined must be agitated. The agitation is necessary since the electrode has an inherent consumption of oxygen and an oxygen-depleted zone forms around the catheter with an unagitated specimen. This phenomenon is generally referred to as the stirring effect. The effect is avoided in the present apparatus since the carrier fluid continuously flows pass the measuring electrode. The so called "oxygen sink" can thus not form.

In the present apparatus, a stripping of the carrier fluid from the dissolved gases to either a partial pressure of nearly zero or to a predetermined partial pressure which can be identical to the anticipated partial pressure in the measuring fluid is carried out following the measuring procedure.

It is particularly advantageous with the apparatus of the present invention to include a bypass through which the stripped carrier fluid or the carrier fluid enriched to a predetermined pressure can be conducted through the measuring means. The bypass, for example, can be provided by a four-way double-L valve or a 3/2 path valve.

BRIEF DESCRIPTION OF THE DRAWINGS

A further description of the present invention will be in conjunction with the attached drawings which illustrates several exemplary embodiments thereof.

DESCRIPTION OF THE PREFERRED EMBODIMENTS

Figure 1:
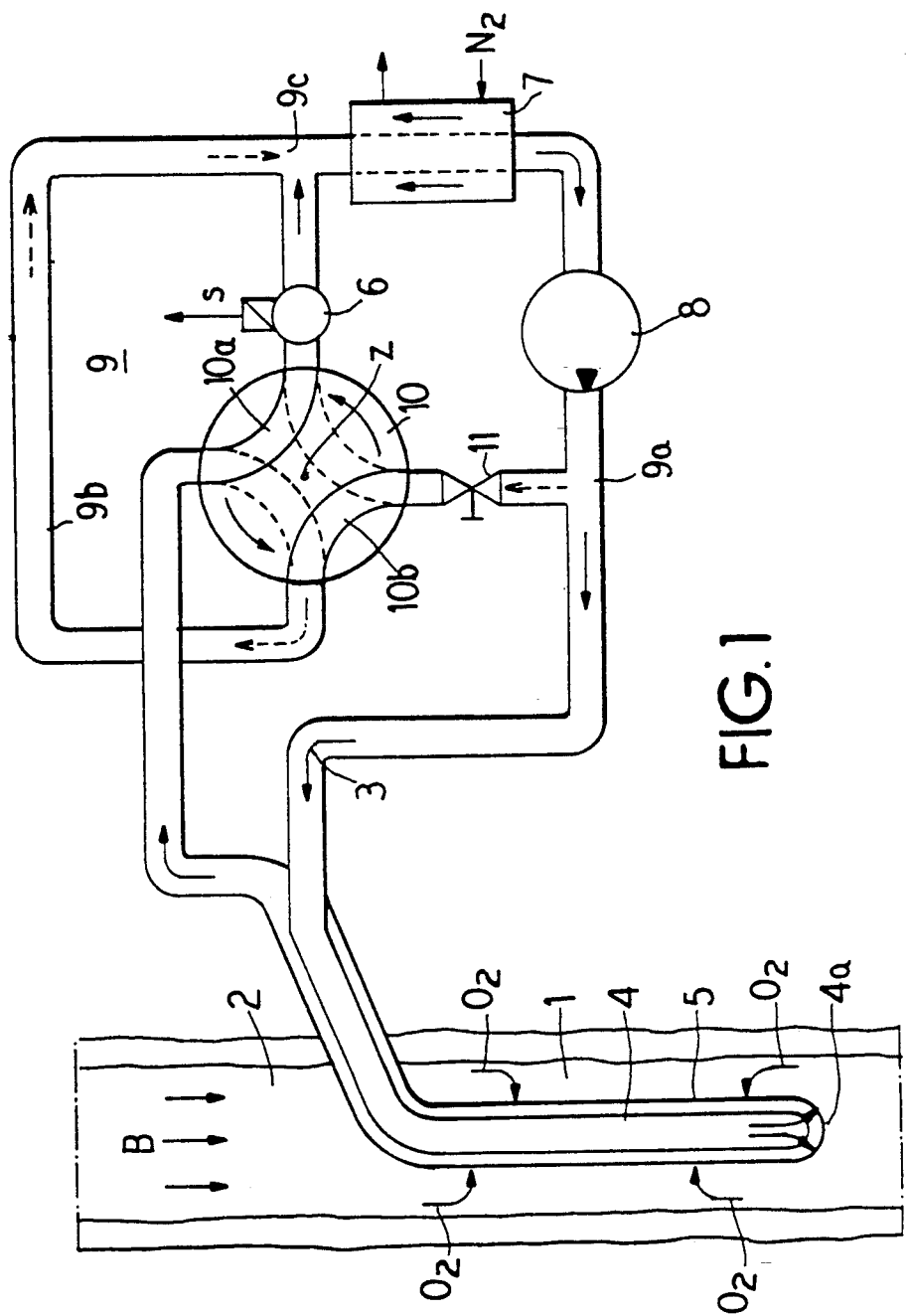
FIG. 1 is a somewhat schematic view of an apparatus for the determination of the partial oxygen pressure in blood.

FIG. 1 shows an example which is particularly suited for continuous, intravascular determination of the partial pressure of oxygen and carbon dioxide in a fluid such as arterial blood B. A double bored, coaxial catheter 1 is provided to be inserted into an artery 2. A carrier fluid 3 consisting of a gas or a liquid is continuously transported through the catheter in a closed circulation.

The carrier fluid 3 may be distilled water which has been freed of oxygen and carbon dioxide before delivery into the catheter 1. It enters into the inner tube 4 of the catheter, flows in the inner tube 4 up to the open end thereof at the catheter tip 4a and flows back into the clearance between the closed end, outer tube 5 and the inner tube 4. The carrier fluid 3 leaving the catheter 1 flows through a branch 10a of a four-way valve 10 consisting of a double-L on-off valve. The carrier fluid is directed to a partial pressure measuring means 6 which also contains a measuring device for $CO_2$ in addition to containing a measuring means for oxygen. For example, the measuring means may consist of a polarographic measuring device. It provides measured signals identified at s. The fluid 3 subsequently enters into a mass transfer unit 7 and is stripped of $O_2$ and $CO_2$ in that unit. To accomplish this, nitrogen gas is conducted through the unit 7 in counter-flow relationship to the carrier fluid. Air can also be employed for this purpose. The carrier fluid 3 is subsequently pumped back into the inside tube 4 of the catheter 1 by means of a compressor or a pump 8.

The oxygen exchange unit 7 can be arranged such that instead of completely stripping the $O_2$ and $CO_2$, the carrier gas is adjusted to a predetermined partial pressure of these two gases. This is of significance particularly for the "compensation" method to be described later.

The apparatus also contains a bypass which is generally identified at reference 9. This bypass 9 leads from a first T-union 9a at the output of the pump 8, through a fine metering valve 11, a branch 10b of the four-way valve 10 and by means of a line segment 9b to a second T-union 9c at the input of the mass transfer unit 7. With the switch position of the four-way valve 10 shown in FIG. 1, and illustrated in solid lines, a bypass is thus provided for the carrier fluid 3 which has been treated in the mass transfer unit 7 and passes through the fine metering valve 11. This fluid flow is marked by the dashed arrows. The carrier fluid conveyed by the pump 8 is thus divided with one part flowing to the catheter 1 and another part flowing to the bypass 9. The fine metering valve 11 is manually set once and remains in the open position. The flow rate of the carrier fluid in the catheter 3 is thus set.

The structure and function of the elements described above is set forth below.

For intravascular partial pressure measurements in arterial blood B, for example, the double bored catheter may have an outside diameter of 1.9 mm. The inner tube 4 may be composed of polytetrafluoroethylene hose which is impermeable to the blood gases to be measured, i.e., oxygen and carbon dioxide. The outer tube 5 is preferably composed of a silicone rubber hose over its entire length and is introduced into the artery 2. The silicone rubber has good permeability for the blood gases but not for the blood B. A relatively large exchange surface for these gases is thus provided. With introduction of the catheter 1 into the oxygen-rich arterial blood B, oxygen and carbon dioxide can thus diffuse through the outer hose 5 into the carrier fluid 3 flowing through the catheter 1, thereby enriching the carrier fluid.

The measuring means 6 is constructed in a known way. It can include oxygen and carbon dioxide sensors built into the wall of a tube section. It can be in the form of a polarographic measuring means for oxygen measurement. Conclusions regarding the partial oxygen pressure and the partial carbon dioxide pressure in the blood B surrounding the catheter 1 can be drawn from the amount of the enrichment. The apparatus thereby differs from known apparatus in that an equilibrium need not be established, but only a stationary condition in order to obtain information about the partial gas pressure of the blood after a short waiting time. By the term "equilibrium" is meant the equality of the partial pressure of the carrier fluid 3 and of the fluid, blood B to be measured. A "stationary condition" is a chronological constancy for the partial pressure of the carrier fluid 3.

In the examples shown in FIG. 1, the mass transfer unit 7 is a capillary tube mass exchanger through which the enriched carrier fluid 3 is pumped. The unit 7 is traversed by nitrogen gas in counterflow relationship with the carrier gas as shown by the arrows in the unit 7. In the exchange unit 7, the carrier fluid 3 again gives off oxygen and carbon dioxide dissolved in it and absorbs nitrogen.

The valve 10 can be turned from the position illustrated by 90° around its axis and can thus be switched into the bypass position shown with broken lines. The bypass 9 enables a fluid sub-stream to be branched off before the catheter 1 by the T-joint 9a and to be conveyed by means of the metering valve 11 and the valve 10 situated in the second position directed into the measuring means 6. This sub-stream thus flows through the elements 8, 9a, 11, 10b, 6, 9c and 7. This presents the possibility of checking the partial pressures of the carrier fluid 3 before and after enrichment for stripping. It is thus possible to carry out a reference measurement, i.e., to check whether, for example, the stripping of the carrier fluid 3 from oxygen and carbon dioxide has been adequately accomplished in the mass transfer unit 7. In order to perform the reference measurement, the volume stream through the bypass 9 is adjusted with the fine metering valve 11, for example, equal to the volume stream through the catheter 1.

In the embodiment shown herein, the measuring means 6 preferably comprises a polarographic electrode for oxygen measurement. A glass electrode can be employed for the carbon dioxide measurement. Both electrodes can be used in parallel or in series. As needed, further electrodes, for example, for electrolytes such as potassium, sodium or calcium compounds can be provided. As is known, the current reduced in the polarographic electrode during the measurement is proportional to the partial pressure of the oxygen in the carrier fluid 3. When, for example, air is allowed to stream through the exchange unit 7 in the bypass position shown in broken lines of the valve 10, instead of nitrogen, the electrode measuring arrangement can be calibrated. By fixing the zero point and the measuring point set by the air calibration, the sensitivity of the electrodes can be checked simply, for example, to check the linear behavior of the measured signal s with respect to the measured variable.

Figure 2:
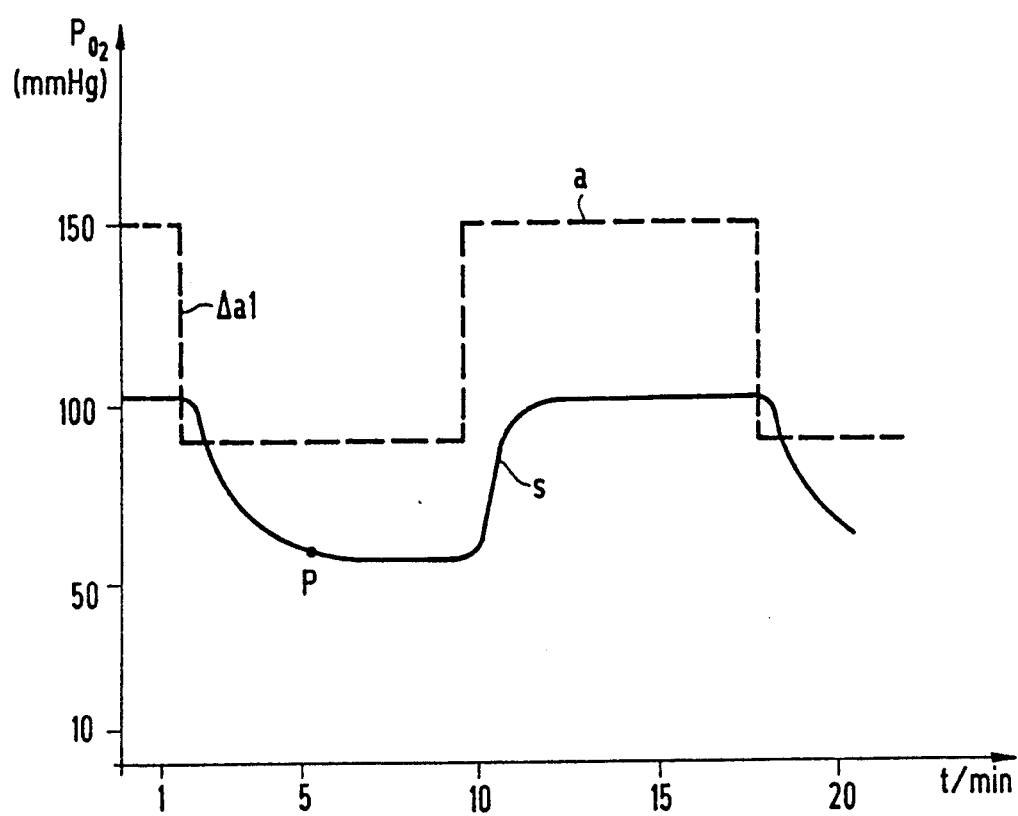
FIG. 2 is a chart illustrating the reaction behavior of the apparatus to discontinuous changes in partial pressures.

FIG. 2 shows the reaction behavior of the apparatus shown in FIG. 1 to changes of the partial oxygen pressure in arterial blood. The electrode output signal s is plotted with an x/t plotter as a function of the time t in minutes. The electrode output signal s is thereby calibrated directly in pressure units, namely in mm of Hg. Signal s thus corresponds to the oxygen partial pressure $pO_2$.

Discontinous changes in partial pressure as shown in FIG. 2 in a broken line curve a. Thus, a change of the partial pressure in a discontinuous manner in the medium surrounding catheter 1 on the order of magnitude of the difference in partial oxygen pressure between arterial and venous blood is registered at the electrode in measuring means 6 after about 15 seconds. The final value after reaching stationary conditions is achieved in the carrier fluid after about 3 minutes. This is identified by a point P. Stationary conditions are present beginning roughly with point P. The partial pressure in the fluid 3 flowing over the catheter 1 is thus quantitatively identified as a measured value.

A clear drop in partial pressure, for example, of oxygen can already be read at the partial pressure change rate after about 15 seconds. For example, an alarm signal for patient monitoring or a signal for other purposes can be derived therefrom. Consequently, there is a possibility for taking counter-measures on behalf of the anethesiologist at this point in time. Moreover, a trend in the partial pressure of the blood gas, for example, an impending insufficient supply for the patient, can also be read with reference to the identified change rate of the partial pressure.

While the invention has been set forth with reference to FIGS. 1 and 2, various modifications are possible within the general scope of the invention, namely, to employ a catheter of double bored construction and to identify the partial pressure of the gases dissolved in the carrier fluid without waiting for an equilibrium to be established. Instead of distilled water as the carrier fluid 3, other liquids or gases can also be employed. The only requirement is that the gases whose partial pressure is to be identified dissolve in the carrier fluid 3.

The use of a gas as a carrier fluid has the advantage that an even faster reaction behavior of the apparatus is obtained than with a liquid. The diffusion in gases occurs significantly faster than in liquids.

When a gas is employed as a carrier fluid, the described apparatus can be utilized, for example, as a high sensitivity system for nitrous oxide measurement in exhaust gases.

In medical technology, particularly for measurements in veins, it is advantageous to use a liquid as a carrier fluid for safety reasons as well as for reasons of miniaturization, i.e., employing a liquid pump instead of a gas compressor. It is also advantageous in medical technology that the apparatus comprises a closed circulating system since sterilization problems do not occur.

In other areas of application, for example, in environmental protection, it would be advantageous to provide remotely controlled rinsing means so that contaminations can be eliminated. The measuring system can thus be used maintenance-free at, for example, measuring locations that are difficult to access.

The employment of the following evaluation unit is able to recognize a trend of the partial pressure enables the integration of the apparatus into for example, an automatic control system in dialysis, in artificial respiration, and in extra-corporeal $CO_2$ elimination.

It is possible to reverse the flow direction through the catheter 1. Furthermore, the outer tube 5 can be selectively permeable for particular gases instead of being permeable for all gases. The upper end, however, can be made of a material which is impenetrable for gases. The inner tube 4 can also be selectively permeable under certain conditions. However, it can also be made integrally permeable.

Figure 3:
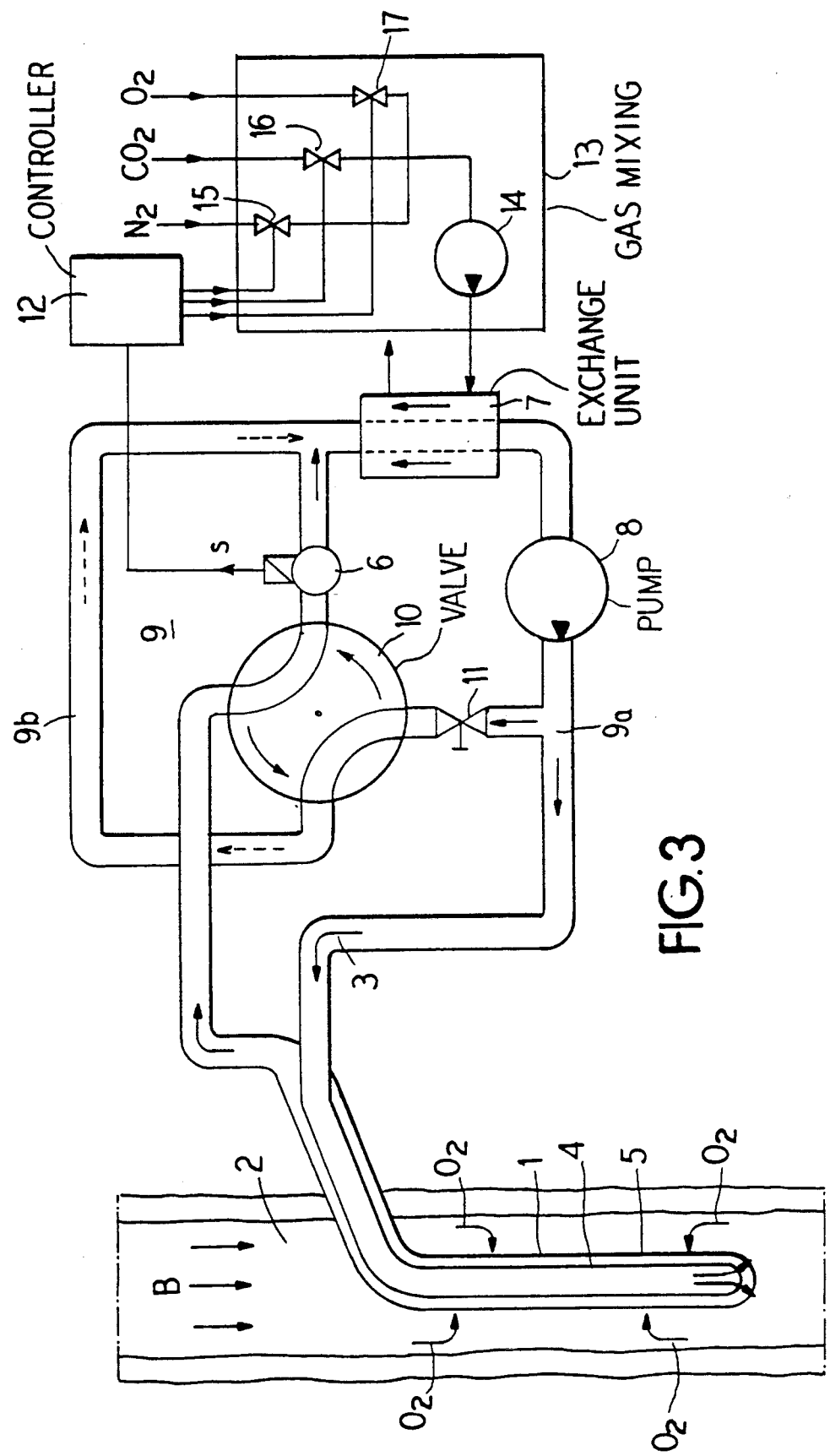
FIG. 3 illustrates a modified form of the present invention which utilizes the compensation method.

FIG. 3 shows an embodiment which operates on a "compensation measuring" method. The mass transit unit 7 in the compensation measuring method can be fed with a gas mixture, in particular of $O_2$, $CO_2$, and $N_2$ which has approximately the same partial oxygen pressure and carbon dioxide partial pressure as the fluid (blood B) to be analyzed. The measurement used for the compensation measuring method of FIG. 3 contains some components in addition to those of FIG. 1. A control is required in the compensation measuring methods since a measured value (the actual value, defined by the gas mixture) is compared to a desired value (the rated value, measured in the fluid) and since the actual value must be constantly approached or followed-up to the rated value. The compensation in the partial pressure measurement is changed such that the oxygen and carbon dioxide partial pressures of the carrier fluid 3 are matched to that of the fluid, the blood B, to be measured.

The $O_2$, $CO_2$ partial pressure of the blood B is thus the rated or fixed value. It is identified and stored in the measuring portion of the four-way valve 10, i.e., in the illustrated switch position 1. The actual value is the $O_2$, $CO_2$ partial pressure of the carrier fluid 3. It is subsequently identified and stored in the bypass portion of the valve 2, i.e., in the switch position 2, turned by 90° from position 1. The same measuring means 6 can be utilized for both measurements. The comparison between actual and rated values occurs in a regulator means 12.

Since it is only deviations between rated and actual value which must be measured in the measuring system and the deviations vary within a substantially smaller frame work than the absolute values, a greater measuring precision can be achieved with the compensation measuring method.

In performing the compensation measuring method, a gas mixing pump 13 is employed whose output side supplies the mass transfer unit 7 with the gas composition to be set. The gas mixing pump 13 has connections to a nitrogen supply, to an oxygen supply and to a carbon dioxide supply. It contains the actual pump unit 14 and final control elements 15, 16 and 17 in the form of valves. Its final control elements 15 to 17 are fed with control signals from the regulating means 12 which, in turn, is fed by the signals s (actual value, rated value) of the measuring means 6. As already noted, the rated value and the actual value are identified in the measuring means 6 by the measuring electrodes for oxygen and carbon dioxide and are employed for the control of the gas mixing pump by means of the control means 12.

When, for example, the oxygen electrode registers an increasing partial oxygen pressure in the blood, this value is compared in the control means 12 to the actual value in the carrier fluid 3. Where a deviation occurs, a signal is forwarded to the gas mixing pump 13. When, for example, the actual value in the carrier fluid 3 is too low, then, the oxygen feed is increased and the nitrogen feed is throttled by the final control elements 17 and 15. This occurs inside the gas mixing pump 13, for example, by means of servo valves. Gas mixing pumps for these purposes are commercially available. This modification based on the compensation measuring method is also operated as a closed circulation system and, thus, continuously.

Figure 4:
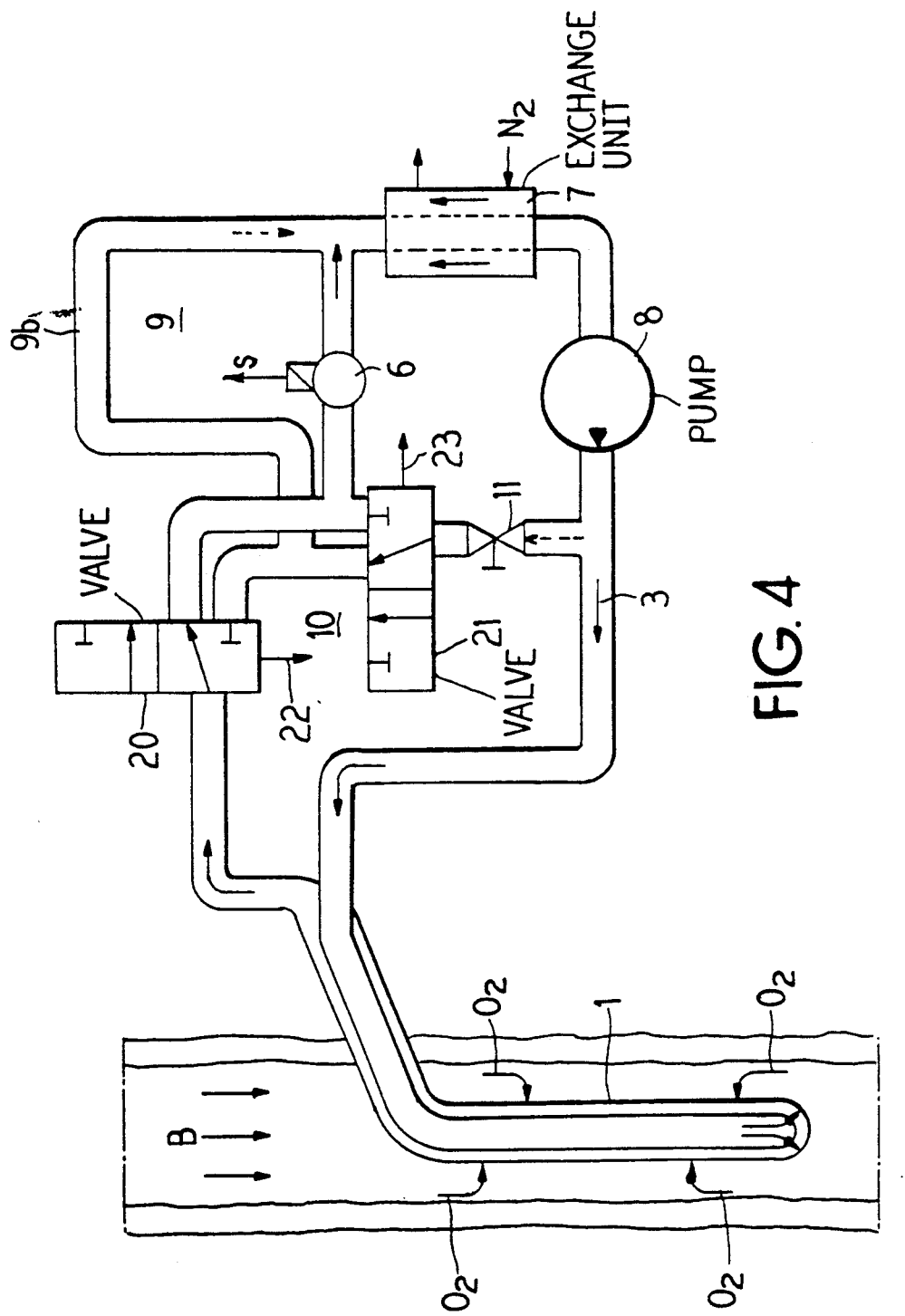
FIG. 4 illustrates an alternative embodiment comprising two switch-over devices which are actuated simultaneously.

The function of the bypass 9 can also be carried out in the manner other than that set forth above. In FIG. 4, for example, the four-way valve 10 can be replaced by two 3/2 way valves 20, 21 connected as shown. Such 3/2 way valves 20, 21 are known, per se, and are commercially available. In the illustrated switch position 1, the apparatus can be switched into a switch position 2 by simultaneous switching in the direction of arrows 22 and 23. This can easily be followed with reference to the symbols indicated in the valves 20 and 21. The valves 20 and 21 represent a first or second switch over means.

Figure 5:
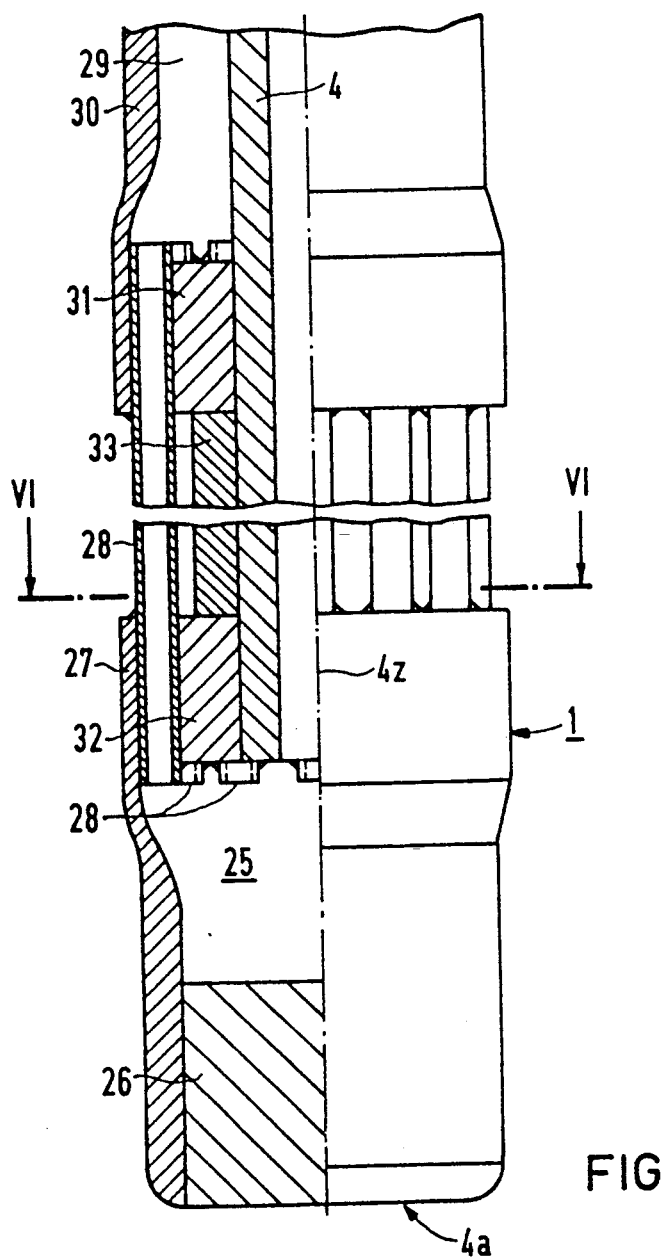
FIG. 5 illustrates a modified form of a catheter, shown partially in plan view and partially in section, illustrating the various capillaries which are employed for gas exchange.
Figure 6:
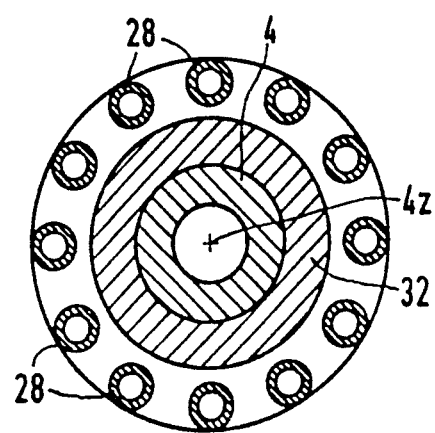
FIG. 6 is a cross-sectional view of the catheter shown in FIG. 5 taken substantially along the line VI—VI.

According to FIGS. 5 and 6, it is possible to divide the annular channel formed between the inner and outer tube 4, 5 into a plurality of individual channels. In the measurement of the blood gas, for example, a capillary tube bundle composed for example of twelve fine polypropylene capillaries can be integrated into the outer tube 5. This embodiment permits local measurements to be carried out and thereby to draw a balance over a full organ in a medical examination in order to acquire data about its oxygen consumption. It is also possible to acquire flow profile data in this way.

According to FIGS. 5 and 6, the lower end of the catheter 1 encompasses an inner tube 4 which discharges into a closed reversing space 25. The space 25 is essentially formed by a stopper 26 and an outer hose 27 drawn thereover. One end of a total of 12 capillaries 28 lead out from the space 25, the capillaries 28 being equally spaced about the central axis $4z$ of the inner tube 4. They thus lie at spacings of about 30°. Their other ends discharge in common into an annular space 29 which is formed from the inner tube 4 and a drawn-on outer tube 30.

Two perforated disks 31 and 32 and a spacing hose 33 inserted therebetween are provided in the region between the spaces 25 and 29 in which the capillaries 28 are situated and serve to fasten the capillaries. The capillaries 28 are introduced into the perforated disks 31 and 32 at their edges. The ends of the hoses 30 or 27 are drawn-over the perforated disks 31 and 32. In order to avoid leaks, the hoses 27 and 30 are glued to the arrangement 31 and 32 in any suitable way.

As noted previously, the flow-through measuring means 6 can be formed by a tube segment into whose wall commercially available sensors for oxygen and carbon dioxide are set. Such a tube segment can be made T-shaped for every sensor.

It will be evident that various modifications can be made to the described embodiments without departing from the scope of the present invention.

We claim as our invention:

1. An apparatus for determining the partial pressure of a gas dissolved in a fluid which comprises:
   a catheter comprising a double bored coaxial catheter having an outer tube and a spaced coaxial inner tube, said outer tube being permeable to said gas,
   fluid circulating means for delivering a continuous flow of a carrier fluid into the space between said inner tube and said outer tube,
   a measuring means downstream of said catheter for determining the partial pressure of said gas in said carrier fluid, and
   a mass transfer unit receiving the gas after said measuring means and arranged to bring the partial pressure of the gas in said carrier fluid to a predetermined value.

2. An apparatus according to claim 1 wherein said outer tube is permeable to more than one of the gases dissolved in said fluid.

3. An apparatus according to claim 1 wherein said outer tube is selectively permeable to one of the gases dissolved in said fluid.

4. An apparatus according to claim 1 wherein the space between the outer and inner tubes is divided into separate channels over at least a portion of the lengths of said tubes.

5. An apparatus according to claim 1 wherein said inner tube is impermeable to said dissolved gas.

6. An apparatus according to claim 1 wherein said fluid circulating means comprises a closed circulating system.

7. An apparatus according to claim 1 wherein said carrier fluid is a liquid.

8. An apparatus according to claim 1 wherein said fluid circulating means comprises a pump located downstream of said mass transfer unit.

9. An apparatus according to claim 1 wherein said measuring means comprises a polarographic electrode.

10. An apparatus according to claim 1 which includes a bypass for diverting a substream of the carrier fluid leaving said mass transfer unit.

11. An apparatus according to claim 10 wherein said bypass includes two T-unions and a metering valve.

12. An apparatus according to claim 1 which includes first valve means for selectively delivering the discharge from said catheter to said measuring means or said mass transfer unit.

13. An apparatus according to claim 12 which includes a second valve means for selectively delivering the discharge pumps from said mass transfer unit to said measuring means.

14. An apparatus according to claim 13 wherein in a first position of said valve means flow is established from said fluid circulating means to said mass transfer unit and back to said fluid circulating means and in a second position flow is established to said measuring means, said mass transfer unit and then back to said fluid circulating means.

15. An apparatus according to claim 14 wherein said switch means are four-way valves.

16. An apparatus according to claim 1 which includes a gas mixing pump connected to said mass transfer unit, and means for introducing controlled amounts of nitrogen, carbon dioxide and oxygen into said pump.

17. An apparatus according to claim 14 which includes means for identifing a standard predetermined gas concentration in said first position and the actual gas concentration in said second position.

18. An apparatus according to claim 1 wherein said mass transfer unit is a gas stripping means.

* * * * *